(12) United States Patent
Pather et al.

(10) Patent No.: US 6,350,470 B1
(45) Date of Patent: Feb. 26, 2002

(54) EFFERVESCENT DRUG DELIVERY SYSTEM FOR ORAL ADMINISTRATION

(75) Inventors: S. Indiran Pather, Plymouth, MN (US); Joseph R. Robinson, Madison, WI (US); Jonathan D. Eichman, Ann Arbor, MI (US); Rajendra K. Khankari, Maple Grove, MN (US); John Hontz, Plymouth, MN (US); Sangeeta V. Gupte, Maple Grove, MN (US)

(73) Assignee: Cima Labs Inc., Minneapolis, MN (US)

( * ) Notice: Subject to any disclaimer, the term of this patent is extended or adjusted under 35 U.S.C. 154(b) by 0 days.

(21) Appl. No.: 09/302,105

(22) Filed: Apr. 29, 1999

Related U.S. Application Data

(60) Provisional application No. 60/083,391, filed on Apr. 29, 1998.

(51) Int. Cl.[7] .............................. A61K 9/24; A61K 9/46
(52) U.S. Cl. ..................... 424/466; 424/465; 424/472; 424/452; 424/489; 514/960
(58) Field of Search ................................ 424/466, 465, 424/464, 451, 489, 472, 452, 458, 463, 490, 474, 468, 461, 462, 480, 481, 482, 494, 496

(56) References Cited

U.S. PATENT DOCUMENTS

| | | | | |
|---|---|---|---|---|
| 3,961,041 A | | 6/1976 | Nishimura et al. ........... 424/35 |
| 4,289,751 A | | 9/1981 | Windheuser ................. 424/35 |
| 4,503,031 A | | 3/1985 | Glassman .................... 424/15 |
| 5,178,878 A | * | 1/1993 | Wehling et al. ............. 424/466 |

OTHER PUBLICATIONS

Eichman, J.D., and Robinson, J.R., "Mechanistic Studies on Effervescent–Induced Permeability Enhancement" Pharm. Res. 15(6):925–30 (1998).

Eichman, J.D., Thesis "Mechanistic Studies on Effervescent–Induced Permeability Enhancement" (catalogued at the University of Wisconsin–Madiosn on Sep. 18, 1998) (on file with the University of Wisconsin–Madison).

K. Sashara et al., Dosage Form Design for Improvement of Bioavailability of Levodopa IV: Possible Causes of Low Bioavailability of Oral Levodopa in Dogs, J. Pharm. Sci., (7)70:730–733 (1981).

K. Sasahara et al., Dosage Form Design for Improvement of Bioavailability of Levodopa III: Influence of Dose on Pharmacokinetic Behavior of Levodopa in Dogs and Parkinsonian Patients, J. Pharm. Sci., (12)69:1374–1378 (1980).

K. Sashara et al., Dosage Form Designe for Improvement of Bioavailability of Levodopa II: Bioavailability of Marketed Levodopa Preparations in Dogs and Parkinsonian Patients, J. Pharm. Sci., (3)69 261–265 (1980).

(List continued on next page.)

*Primary Examiner*—James M. Spear
(74) *Attorney, Agent, or Firm*—Lerner, David, Littenberg, Krumholz & Mentlik, LLP

(57) ABSTRACT

The pharmaceutical compositions of the present invention comprise orally administerable dosage forms that use effervescence as a penetration enhancer for drugs known, or suspected, of having poor bioavailability. Effervescence can occur in the stomach, once the tablet or other dosage form is ingested. In addition to effervescence in the stomach, or as alternative technique, by the use of appropriate coatings and other techniques, the effervescence can occur in other parts of the gastrointestinal tract, including, but not limited to, the esophagus, duodenum, and colon. The site of effervescence and drug release is chosen to correspond with the segment of the gastrointestinal tract displaying maximal absorption of the formulated drug, or to gain some other therapeutic advantage.

59 Claims, 1 Drawing Sheet

OTHER PUBLICATIONS

K. Sasahara et al., Dosage form Design for Improvement of Bioavailability of Levodopa V: Absorption and Metabolism of Levodopa in Intestinal Segments of Dogs, J. Pharm. Sci., (10)70 1157–1160 (1981).

K. Nishimura et al. Dosage Form Design for Improvement of Bioavailibility for Levodopa VI: Formulation of Effervescent Enteric–Coated Tablets, J. Pharm. Sci., (7)73 942–946 (1984).

* cited by examiner

EFFERVESCENT DRUG DELIVERY SYSTEM FOR ORAL ADMINISTRATION

The present application claims benefit of U.S. Provisional Patent Application No. 60/083,391, filed Apr. 29, 1998, the disclosure of which is hereby incorporated by reference.

BACKGROUND OF THE INVENTION

Many orally-administered drugs display poor bioavailability when administered in conventional dosage forms, i.e., the rate and extent to which the drugs are absorbed is less than desirable. With several drugs, absorption may be as little as 30% or less of the orally administered dose. To compensate for this effect, a very large dose is often administered so that absorption of the therapeutically required quantity of the drug can occur. This technique may prove costly with expensive drugs; and the nonabsorbed drug may also have undesirable side effects within the gastrointestinal tract. In addition, poorly absorbed drugs often display large inter- and intrasubject variability in bioavailability. See Aungst, B. J., J. Pharm. Sci., 82:979–987, 1993. Specific examples (with the average bioavailability given in parentheses) include methyldopa (25%) with a range of 8% to 62%. See Kwan, K. C., Folz, E. L., Breault, G. O., Baer, J. E., Totaro, J. A., J. Pharmacol. Exp. Ther., 198:264–277, 1976; and nalbuphine (approximately 17%) with a range of 6% to 40%. See Lo. M.-W, Schary, W. L., Whitney, C. C., Jr., J. Clin. Pharmacol., 27:866–873, 1987. Such variation in the amount of drug absorbed does not allow for good control of the disease condition.

To improve the bioavailability of poorly absorbed drugs, penetration enhancers have also been employed. However, many of the penetration enhancers referred to in the current literature damage the absorbing tissues and thus are not a practical solution to the problem of poor bioavailability. In fact, it has been suggested that the damage to the mucosa caused by these agents may be the factor responsible for the improved absorption. See LeCluyse, E. L. and Sutton, S. C., Advanced Drug Delivery Reviews, 23:163–183, 1997.

Other techniques which have been employed to improve bioavailability include using enteric coated tablets having effervescence to rapidly dissolve or disperse the dosage form in the stomach. See U.S. Pat. Nos. 4,503,031; 4,289,751; and 3,961,041.

SUMMARY OF THE INVENTION

The pharmaceutical compositions of the present invention comprise orally administerable dosage forms that use effervescence as a penetration enhancer for drugs known, or suspected, of having poor bioavailability. Effervescence can occur in the stomach, once the tablet or other dosage form is ingested. In addition to effervescence in the stomach, or as alternative technique, by the use of appropriate coatings and other techniques, the effervescence can occur in other parts of the gastrointestinal tract, including, but not limited to, the esophagus, duodenum, intestinal and colon. The site of effervescence and drug release is chosen to correspond with the segment of the gastrointestinal tract displaying maximal absorption of the formulated drug, or to gain some other therapeutic advantage. Desirably, such site is not in the mouth of the subject.

DETAILED DESCRIPTION OF THE PREFERRED EMBODIMENTS

Figure 1:
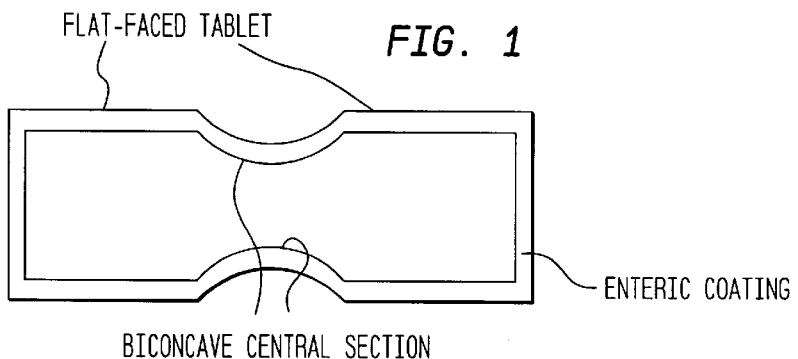
FIG. 1. is an enlarged top plan view of a tablet which has a bioconcaved shaped.

The pharmaceutical compositions of the present invention comprise orally administerable medicaments in combination with an effervescent as a penetration enhancer for influencing absorption of a drug in the gastrointestinal tract. Effervescence leads to an increase in the rate and/or the extent of absorption of the drugs that are known or suspected of having poor bioavailability. It is believed that such increase can rise from one or all of the following mechanisms:

1. reducing the thickness and/or the viscosity of the mucus layer which is present adjacent to the gastrointestinal mucosa;
2. alteration of the tight junctions between cells, thus promoting absorption through the paracellular route;
3. inducing a change in the cell membrane structure, thus promoting transcellular absorption;
4. increasing the hydrophobic environment within the cellular membrane.

The present dosage forms include an amount of effervescent agent effective to aid in penetration of the drug in the gastrointestinal tract. The amount of effervescent employed must not merely permit rapid dispersion of the medicament in the gastrointestinal tract, but must aid in penetration of the drug across the gastrointestinal mucosa. The formulations of the present invention may be distinguished from other effervescent formulation that are enteric coated on the basis of the amount of effervescent material that they contain. Prior formulations contain approximately half to a quarter as much bicarbonate as drug on a weight basis (together with a proportionate amount of acid). In these cases, the small amount of effervescent couple serves only to rapidly disintegrate the tablet.

The dosage forms of the present invention should preferably contain at least twice as much sodium bicarbonate (or an equivalent amount of other base) as drug (on a weight basis) together with the proportionate amount of an appropriate acid for generating the effervescent reaction. More preferably the present dosage forms should contain at least three times as much sodium bicarbonate as drug (on a weight basis) together with the proportionate amount of an appropriate acid. These high concentrations of effervescent couple are needed to generate effervescence in sufficient amounts to promote permeability and absorption of the drug.

Preferably, the effervescent is provided in an amount of between about 5% and about 95% by weight, based on the weight of the finished tablet, and more preferably in an amount of between about 30 to about 60%. However, the amount of effervescent agent must be optimized for each specific drug.

The term "effervescent penetration enhancer" includes compounds which evolve gas. The preferred effervescent penetration enhancers evolve gas by means of a chemical reaction which takes place upon exposure of the effervescent penetration enhancer to water and other fluids. Such water-activated materials must be kept in a generally anhydrous state and with little or no absorbed moisture or in a stable hydrated form, since exposure to water will prematurely disintegrate the tablet. The acid sources may be any which are safe for human consumption and may generally include food acids, acid and hydrite antacids such as, for example, citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like.

The effervescent penetration enhancers of the present invention is not limited to those which are based upon a reaction which forms carbon dioxide. Reactants which evolve oxygen or other gases and which are safe for human consumption are also considered within the scope of the present invention.

The present dosage forms may also include in amounts additional to that required for effervescence a pH adjusting substance. For drugs that are weekly acidic or weakly basic, the pH of the aqueous environment can influence the relative concentrations of the ionized and the unionized forms of the drug present in solution, according to the Henderson-Hasselbach equation. Th pH of solutions in which an effervescent couple with equimolar amounts of base and acid has dissolved is slightly acidic due to the evolution of $CO_2$. While it is impractical and may not be desirable to change the pH of the contents of the small intestine, it is, nevertheless, possible to alter the pH of the local environment (intestinal contents in immediate contact with the tablet and any drug that may have dissolved from it). This is achieved by incorporating in the tablet certain pH adjusting substances. Thus, the relative proportions of the ionized and unionized forms of the drug may be controlled.

In this way the system can be optimized for each specific drug under consideration: if the drug is known, or suspected, to be absorbed through the cell membrane (transcellular absorption), it would be most appropriate to alter the pH of the local environment to a level that favors the unionized form of the drug. Conversely, if the ionized form is more readily dissolved the local environment should favor ionization. Thus, for fentanyl, as a nonlimiting example, the pH is adjusted to neutral (or slightly higher) since the pKa is 7.3. At this pH, the aqueous solubility of this poorly water-soluble drug is not compromised unduly, yet allowing a sufficient concentration of the drug to be present in the unionized form. This facilitates the permeation enhancement brought about by effervescence. In the case of prochlorperazine (pKa=8.1), a slightly higher pH is required.

Suitable pH adjusting substance for use in the present invention include any weak acid or weak base (in amounts additional to that required for effervescence) or, preferably, any buffer system that is not harmful to the gastrointestinal mucosa. These include, but are not limited to, any of the acids or bases previously mentioned as the effervescent components, sodium carbonate, potassium carbonate, potassium carbonate, disodium hydrogen phosphate, sodium dihydrogen phosphate, and the equivalent potassium salts.

The active agents suitable for use in the present invention preferably includes any drug that displays poor bioavailability, slow absorption or long $t_{max}$. These active ingredients include small molecule drugs, nutritional supplements (such as vitamins and minerals), proteins and peptides and other substances of biological origin. Examples of such drugs include, but are not limited to, the following:

| Drug | Bioavailability (%) |
|---|---|
| Acyclovir | 15–30 |
| Auranofin | 15–25 |
| Bretylium | 23 ± 9 |
| Cyclosporine | 23 ± 7 |
| Cytarabine | 20 |
| Doxepin | 27 ± 10 |
| Doxorubicin | 5 |
| Hydralazine | 16–35 |
| Ketamine | 20 ± 7 |
| Labetalol | 18 ± 5 |
| Mercaptopurine | 12 ± 7 |
| Methyldopa | 25 ± 16 |
| Nalbuphine | 25 ± 16 |
| Naloxone | 2 |
| Pentoxifylline | 19 ± 13 |
| Pyridostigmine | 14 ± 3 |
| Terbutaline | 14 ± 2 |
| Verapamil | 22 ± 8 |
| Riboflavin | 11 |
| Atenolol | 50 |

Pharmaceutical ingredients suitable for use in the present dosage forms may include, without limitation, analgesics, anti-inflammatories, antipyretics, antibiotics, antimicrobials, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers; peptides, proteins, oligonucleotides and other substances of biological origin, and combinations thereof. Also encompassed by the terms "active ingredient(s)", "pharmaceutical ingredient(s)" and "active agents" are the drugs and pharmaceutically active ingredients described in *Mantelle*, U.S. Pat. No. 5,234,957, in columns 18 through 21. That text of Mantelle is hereby incorporated by reference. Alternatively or additionally, the active ingredient can include drugs and other pharmaceutical ingredients, vitamins, minerals and dietary supplements as the same are defined in U.S. Pat. No. 5,178,878, the disclosure of which is also incorporated by reference herein.

The dosage forms preferably contain materials that aid in releasing the drug in a specific section of the gastrointestinal tract, thus promoting site-specific delivery. There are various mechanisms by which such materials promote site-specific delivery and this invention is not limited to any one mechanism. For example, the material may be metabolized by enzymes present in a specific part of the gastrointestinal tract, thus releasing the drug in that section.

The materials used to promote site-specific absorption may preferably be included as coatings and/or as matrix materials. If a coating is used, it may be applied to the entire dosage form or to the individual particles of which it consists. Coating materials may be used to prevent the release of the active agent before the dosage form reaches the site of more efficient absorption.

The coating can also be used in conjunction with an effervescence to cause the effervescence to occur at specific areas of the gastrointestinal tract. Nonlimiting examples or coatings used in the present invention include: cellulose derivatives including cellulose acetate phthalate (CAP); shellac and certain materials sold under the trademark Eudragit™ (various grades may be used in specific combinations). Hydroxypropylmethyl cellulose phthallate in a grade that dissolves at pH 5 is the preferred coating material.

Precoating materials may also be used in the present invention. Nonlimiting examples include cellulose derivatives such as methylcellulose, hydroxypropyl cellulose, hydroxypropyl methylcellulose or combinations and certain materials sold under the trademark Eudragit™ (various grades which may be combined). Hydroxypropylmethyl cellulose phthallate in a grade that dissolves at pH 5 is the preferred coating material.

Other materials may be used to aid in site specific delivery, and include, for example, sugars, polysaccharides, starches, polymers, etc. These compounds may be included as coatings or as matrix materials and aid in releasing the drug in specific sections of the gastrointestinal tract, thus promoting site-specific delivery.

Other ingredients or techniques may preferably be used with the present dosage forms to enhance the absorption of the pharmaceutical ingredient, to improve the disintegration profile, and/or to improve the organoleptic properties of the material and the like. These include, but are not limited to, the use of additional chemical penetration enhancers, which are referred to herein as noneffervescent penetration enhancers; absorption of the drug onto fine particles to promote absorption by specialized cells within the gastrointestinal tract (such as the M cells of Peyer's patches); ion pairing or complexation; and the use of lipid and/or surfactant drug carriers. The selected enhancement technique is preferably related to the route of drug absorption, i.e., paracellular or transcellular.

A bioadhesive polymer may preferably be included in the drug delivery device to increase the contact time between the dosage form and the mucosa of the most efficiently absorbing section of the gastrointestinal tract. See Jonathan D. Eichman, "Mechanastic Studies on Effervescent-Induced Permeability Enhancement," University of Wisconsin-Madison (1997), hereby incorporated by reference. Nonlimiting examples of known bioadhesives used in the present invention include: carbopol (various grades), sodium carboxy methylcellulose, methylcellulose, polycarbophil (Noveon AA-1), hydroxypropyl methylcellulose, hydroxypropyl cellulose, sodium alginate, and sodium hyaluronate.

Disintegration agents may also be employed to aid in dispersion of the drug in the gastrointestinal tract. Disintegration agents include any pharmaceutically acceptable effervescent agent. In addition to the effervescence-producing disintegration agents, a dosage form according to the present invention may include suitable noneffervescent disintegration agents. Nonlimiting examples of disintegration agents include: microcrystalline cellulose, croscarmelose sodium, crospovidone, starches and modified starches.

Apart from the effervescent material within the tablet, some additional effervescent components or, alternatively, only sodium bicarbonate (or other alkaline substance) may be present in the coating around the dosage form. The purpose of the latter effervescent/alkaline material is to react within the stomach contents and promote faster stomach emptying.

The drug delivery device may be in the form of a tablet, granules, pellets or other multiparticulates, capsules that can contain the drug in the form of minitablets, beads, or a powder, or any other suitable dosage form.

If tablets are used, they may be matrix tablets; layered tablets in which the various components are separated in different layers to optimize their benefits; or other specialized forms of tablets, including nonconventional shapes and geometric arrangements. One example of a nonconventional shape is a flat-faced tablet with a biconcave central zone, as depicted in FIG. 1. The outer, thicker part of the tablet may contain the mucoadhesive material while the inner, thinner segment may contain the drug and effervescent components. This arrangement allows drug release to a segment of the gastrointestinal mucosa in close proximity to the point at which the tablet is attached to the mucosa.

Figure 2:
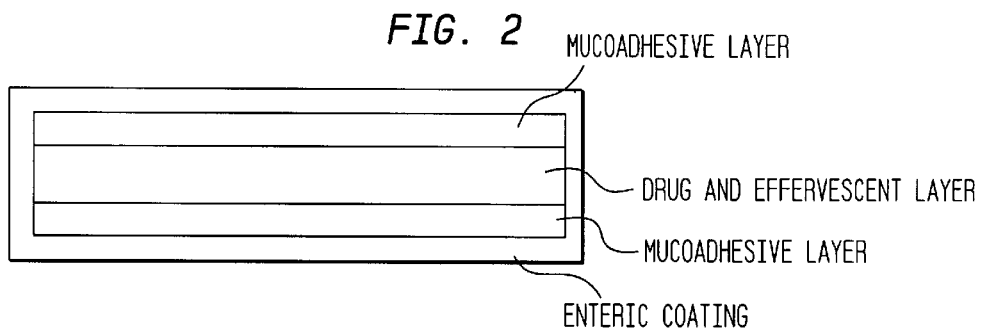
FIG. 2. is an enlarged side view of an enteric coated multilayered tablet.

The drug and/or the effervescent material could be present in a sustained release matrix. The whole tablet may consist of this matrix or the matrix may be confined to one, or more, layers of a multilayered tablet. FIG. 2 depicts a multilayered tablet with a central layer containing the drug and optional effervescent material; and two mucoadhesive layers. The tablet would adhere to the mucosa irrespective of its spatial orientation within the intestine.

Figure 3:
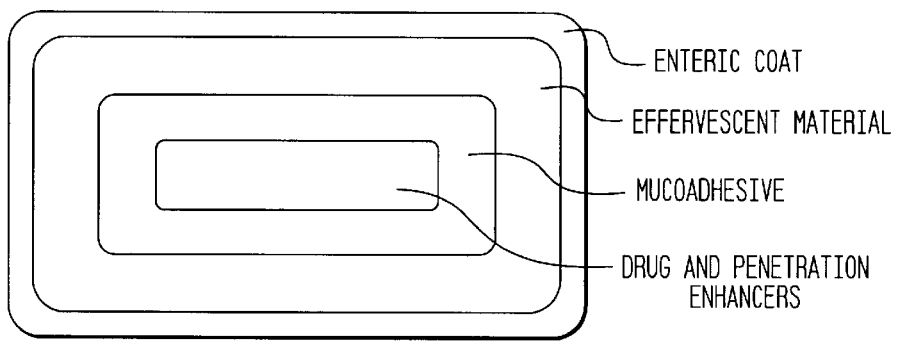
FIG. 3. is an enlarged top view of an enteric coated multilayered tablet, which depicts the effervescent external to the mucous adhesive layer.
Figure 4:
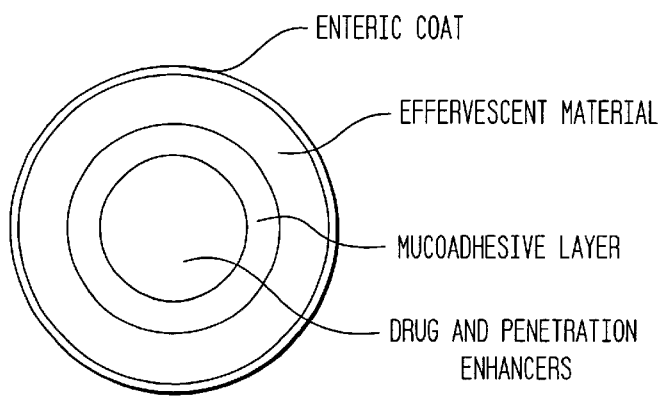
FIG. 4. is an enlarged top view of an enteric coated multilayered pellet, which depicts the effervescent external to the mucous adhesive layer.

FIGS. 3 and 4 depict the effervescent layer external to the mucoadhesive layer of each dosage form. FIG. 3 depicts a multilayered tablet in which a central core is completely surrounded by each subsequent layer. Such a tablet may be prepared by a compression coating technique. A similar physical arrangement of layers can also be achieved in a spheroid or pellet which may be prepared by extrusion and spheronization, layering, coating or any combination of these techniques. (See FIG. 4.) The effervescence will cause a thinning of the mucus layer from the gastrointestinal segment, thus facilitating adhesive of the dosage form to the cellular surface rather than to the mucus layer. This arrangement promotes better absorption of the drug.

Tablets can be manufactured by wet granulation, dry granulation, direct compression or any other tablet manufacturing technique. The tablet may be a layered tablet consisting of a layer of the active ingredients set forth above in layers of diverse compositions. In accordance with the present invention, the tablet size is preferably up to about ¾". In accordance with the present invention, the multiparticulate size is preferably up to about 3 mm. In accordance with the present invention, the tablet hardness is preferably between about 5N and 100N.

Excipient fillers can be used in connection with the present invention to facilitate tableting. Nonlimiting examples of fillers include: mannitol, dextrose, lactose, sucrose, and calcium carbonate.

Pellets or other multiparticulates may be manufactured by granulation, layering techniques, extrusion and spheronization or other pellet manufacturing methods. The multiparticulates are then coated with an enteric coating material as described for tablets. The coating is preferably done in a fluid bed coater. The preferred, but nonlimiting, coating material is hydroxypropylmethyl cellulose in a grade that dissolves at pH 5. The multiparticulates are then packed into capsules.

The granules may be made by a wet granulation process or a dry granulation process. When wet granulation is used, isopropyl alcohol, ethyl alcohol or other nonaqueous granulating agent is used. Low moisture content grades of these organic solvents are used.

Dry granulation may be achieved through slugging or chilsonation. Layering may be done in a fluid bed apparatus or coating pan. Nonaqueous binders are used to aid the adherence of the added material (drug, effervescent penetration enhancer and excipients) to the starting material. Nonlimiting examples of the starting material or cores are nonpareils (sucrose) or microcrystalline cellulose seeds.

The preferred technique for the manufacture of multiparticulates is extrusion and spheronization. The beads contain the drug, effervescent couple (as previously described), a fine particle diluent which also aids in the formation of the beads (examples are lactose and mannitol) and a spheronization aid such as microcrystalline cellulose. The preferred grade of the latter is Avicel RC 591 which contains sodium carboxymethyl cellulose as an additional ingredient. For this formulation, a nonaqueous solvent is used. Nonlimiting examples of nonaqueous solvents are isopropanol and ethanol. Low moisture content grades are used.

The alternate (and preferred) formulation is to manufacture two populations of beads, one containing the acid component and the other the alkaline component of the effervescent couple. Each population of beads contains similar drug concentrations and can be manufactured using water. Care should be taken to ensure that each population of beads has a similar size range and a similar density. Equal densities may be achieved by the incorporation of a nontoxic material of high density to the population of beads that would, otherwise, have had a lower density. A nonlimiting example of such a material is barium sulfate. Equivalence of size and density facilitates the achievement of similar emptying rates of the beads from the stomach once the dosage forms are consumed by the subject. When the beads come into contact with the intestinal fluids, the coating dissolves and the close proximity of the beads to each other allows the effervescent reaction to occur in situ.

The coating applied to the dosage forms of the present invention must be performed with precision to avoid pinhole faults since water penetration through such faults leads to rapid and premature disintegration of the tablet. Such coating can be performed by one skilled in the art who, additionally, takes precautions to limit abrasion and chipping of the partially formed coat during the coating process. A fluid bed coater, pan coater or other coating apparatus may preferably be used.

The invention will be further described by reference to the following detailed examples. These examples are provided for the purposes of illustration only, and are not intended to be limiting unless otherwise specified.

EXAMPLE 1

RIBOFLAVIN

| INGREDIENTS | mg/TABLET |
|---|---|
| Riboflavin, USP | 5 |
| Silicified Microcrystalline Cellulose | 19.7 |
| Sodium Bicarbonate | 18.2 |
| Citric Acid, Anhydrous | 13 |
| Crospovidone | 3 |
| Magnesium Stearate | 0.9 |
| Colloidal Silicon Dioxide | 0.5 |
| TOTAL | 60 |

The tablets were compressed to a hardness of 50 N using $3/16$ inch concave punches. The tablets had a friability of less than 0.25%. Coating solution was prepared according to the following formula:

| INGREDIENTS | WEIGHT (gm) |
|---|---|
| Hydroxypropylmethyl cellulose phthallate | 418.5 |
| Triethylcitrate | 31.5 |
| Ethanol | 2025.0 |
| Acetone | 2025.0 |
| TOTAL | 4500.0 |

Using a fluidized bed coater, the tablets were coated to a 15% weight gain. Care was taken to fluidize the bed sufficiently so that agglomeration of the tablets did not occur during coating but excessive movement was avoided to minimize chipping of the tablets or abrasion of the coating material.

EXAMPLE 2

ATENOLOL

| INGREDIENTS | mg/PER TABLET |
|---|---|
| Atenolol | 7.143 |
| Sodium bicarbonate | 15.000 |
| Citric acid | 10.714 |
| Silicified microcrystalline cellulose | 26.043 |
| Magnesium stearate | 0.900 |
| Silicon dioxide | 0.200 |
| TOTAL | 60.000 |

The tablets were compressed using $3/16$ inch concave punches to a hardness of 40 N. The tablets were coated with hydroxypropylmethyl cellulose phthallate solution as described above to a weight gain of 15%. Seven tablets were packed into a size 0 elongated capsule to form the final dosage form.

EXAMPLE 3

ATENOLOL POPULATION 1

| INGREDIENTS | mg PER CAPSULE |
|---|---|
| Atenolol | 25 |
| Sodium bicarbonate | 150 |
| Lactose | 37 |
| Avicel RC 591 | 38 |
| Water | Qc |
| TOTAL | 250 |

The dry powders were blended together. Water was slowly added with mixing until a wet mass that was plastic (but not tacky) was formed. The wet mass was passed through an extruder. The extruded material was spheronized for 3 minutes. The beads that were formed were air dried for one hour and then dried in an oven at 35° C. overnight. The beads were sieved to remove large particles and fines.

EXAMPLE 4

ATENOLOL POPULATION 2

| INGREDIENTS | mg PER CAPSULE |
|---|---|
| Atenolol | 25 |
| Citric acid | 107 |
| Lactose | 80 |
| Avicel RC 591 | 38 |
| Water | Qs |
| TOTAL | 250 |

Population 2 was made in a similar fashion to population 1. Each population of beads was separately coated to a 20% weight gain in a fluidized bed coater using the previously described coating solution. Two hundred and fifty milligrams of each population of beads was filled into size 0 elongated capsules and this formed the final dosage form.

Various modifications of the invention described herein will become apparent to those skilled in the art. Such modifications are intended to fall within the scope of the appending claims.

We claim:

1. A dosage form for delivery of a therapeutically effective amount of a drug to a target area in the gastrointestinal tract of a mammal; comprising:
   (a) a therapeutically effective amount of a drug;
   (b) at least one effervescent penetration enhancer; wherein said at least one effervescent penetration enhancer is present in an amount sufficient to increase the penetration of said drug across said target area of said gastrointestinal tract to permit delivery of a therapeutically effective amount of said drug;
   (c) a pH adjusting substance comprising an acid or a base; and
   (d) an enteric coating maintained over said drug, said at least one effervescent penetration enhancer and said pH adjusting substance; wherein said enteric coating prevents the release of said drug, said at least one effervescent penetration enhancer and said pH adjusting substance until a time at which said dosage form reaches said target area in said gastrointestinal tract.

2. The dosage form of claim 1, wherein said amount of said at least one effervescent penetration enhancer is equal to about two times the amount of said drug.

3. The dosage form of claim 1, wherein said amount of said at least one effervescent penetration enhancer is equal to about three times the amount of said drug.

4. The dosage form of any one of claims 1–3, further comprising at least one noneffervescent penetration enhancer.

5. The dosage form of any one of claims 1–3 further comprising at least one disintegration agent, wherein said disintegration agent causes the rapid dispersion of said drug to said target area of said gastrointestinal tract.

6. The dosage form of any of claims 1–3, wherein said enteric coating comprises a material that reacts with an enzyme present in said target area of said gastrointestinal tract to release said drug, said effervescent penetration enhancer and said pH adjusting substance.

7. The dosage form of any one of claims 1–3, wherein said dosage form is a tablet.

8. The dosage form of any one of claims 1–3, wherein said dosage form is a capsule.

9. The dosage form of any one of claims 1–3, wherein said dosage form is in the form of granules.

10. The dosage form of any one of claims 1–3, wherein said dosage from is in the form of pellets.

11. The dosage form of claim 7, wherein said tablet contains a biconcave zone central to two outer zones; wherein said drug, said effervescent penetration enhancer and said pH adjusting substance are located in said biconcave zone.

12. The dosage form of claim 11, wherein a bioadhesive is contained in said two outer zones.

13. The dosage form of claim 1, wherein said effervescent penetration enhancer comprises a pharmaceutically acceptable effervescent couple; said effervescent couple comprising an acid or equivalent thereof and a base or equivalent thereof.

14. The dosage form of claim 13, wherein said base of said effervescent couple is sodium bicarbonate.

15. The dosage form of claim 13, wherein, in said effervescent couple, said base or equivalent thereof is present in an amount equal to about two times the amount of said drug; and said acid of said effervescent couple is present in an amount approximately equimolar to said base of said effervescent couple.

16. The dosage form of claim 13, wherein, in said effervescent couple, said base or equivalent thereof is present in an amount equal to about two times the amount of said drug; and said acid of said effervescent couple is present in an amount approximately equimolar to said base of said effervescent couple.

17. The dosage form of claim 1, wherein said drug is a drug that displays poor bioavailability in said gastrointestinal tract.

18. A dosage form for delivery of a therapeutically effective amount of a drug to a target area in the gastrointestinal tract of a mammal; comprising:
   (a) a therapeutically effective amount of a drug;
   (b) at least one effervescent penetration enhancer; wherein said at least one effervescent penetration enhancer is present in an amount sufficient to increase the penetration of said drug across said target area of said gastrointestinal tract to permit delivery of a therapeutically effective amount of said drug;
   (c) a bioadhesive; wherein said bioadhesive increases contact time between said drug and a mucosa layer of said target area; and
   (d) an enteric coating maintained over said drug, said at least one effervescent penetration enhancer and said bioadhesive; wherein said enteric coating prevents the release of said drug and said at least one effervescent penetration enhancer and the exposure of said bioadhesive until a time at which said dosage form reaches said target area in said gastrointestinal tract.

19. The dosage form of claim 18, wherein said amount of said at least one effervescent penetration enhancer is equal to about two times the amount of said drug.

20. The dosage form of claim 18, wherein said amount of said at least one effervescent penetration enhancer is equal to about three times the amount of said drug.

21. The dosage form of any one of claims 18–20, further comprising a pH adjusting substance.

22. The dosage form of claim 18, wherein said bioadhesive is contained in a portion of said dosage form external to said drug.

23. The dosage form of any one of claims 18–20, further comprising at least one noneffervescent penetration enhancer.

24. The dosage form of any one of claims 18–20, further comprising at least one disintegration agent, wherein said disintegration agent causes the rapid dispersion of said drug to said target area of said gastrointestinal tract.

25. The dosage form of any one of claims 18–20, wherein said enteric coating comprises a material that reacts with an enzyme present in said target area of the gastrointestinal tract to release said drug and said effervescent penetration enhancer.

26. The dosage form of any one of claims 18–20, wherein said dosage form is a tablet.

27. The dosage form of any one of claims 18–20, wherein said dosage form is a capsule.

28. The dosage form of any one of claims 18–20, wherein said dosage form is in the form of granules.

29. The dosage form of any one of claims 18–20, wherein said dosage form is in the form of pellets.

30. The dosage form of claim 26, wherein said tablet contains a biconcave zone central to two outer zones; wherein said drug and said effervescent penetration enhancer are located in said biconcave zone.

31. The dosage form of claim 30, wherein said bioadhesive is contained in said two outer zones.

32. The dosage form of claim 18, wherein said effervescent penetration enhancer comprises a pharmaceutically acceptable effervescent couple; said effervescent couple comprising an acid or equivalent thereof and a base or equivalent thereof.

33. The dosage form of claim 32, wherein said base is sodium bicarbonate.

34. The dosage form of claim 32, wherein said base or equivalent thereof is present in an amount equal to about two times the amount of said drug; and said acid is present in an amount approximately equimolar to said base.

35. The dosage form of claim 32, wherein said base or equivalent thereof is present in an amount equal to about three times the amount of said drug; and said acid is present in an amount approximately equimolar to said base.

36. The dosage form of claim 32, wherein said drug is a drug that displays poor bioavailability in said gastrointestinal tract.

37. A dosage form for delivery of a therapeutically effective amount of a drug to a target area in the gastrointestinal tract of a mammal; comprising:
   a therapeutically effective amount of a drug;
   at least one effervescent penetration enhancer; wherein said at least one effervescent penetration enhancer is present in an amount sufficient to increase the penetration of said drug across said target area of said gastrointestinal tract to permit delivery of a therapeutically effective amount of said drug;
   at least one noneffervescent penetration enhancer; and
   an enteric coating maintained over at least one of said drug, said at least one effervescent penetration enhancer and said at least one noneffervescent penetration enhancer; wherein said enteric coating prevents the release of said drug, said at least one effervescent penetration enhancer or said at least one noneffervescent penetration enhancer until a time at which said dosage form reaches said target area in said gastrointestinal tract;
   wherein said dosage form is in the form of a capsule, granules, or pellets.

38. The dosage form of claim 37, wherein said amount of said at least one effervescent penetration enhancer is equal to about two times the amount of said drug.

39. The dosage form of claim 37, wherein said amount of said at least one effervescent penetration enhancer is equal to about three times the amount of said drug.

40. The dosage form of any one of claims 37–39, further comprising a pH adjusting substance.

41. The dosage form of any one of claims 37–39, further comprising a bioadhesive, wherein said bioadhesive increases contact time between said drug and a mucosa layer of said target area.

42. The dosage form of claim 41, wherein said bioadhesive is contained in a portion of said dosage form external to said drug.

43. The dosage form of any one of claims 37–39, further comprising at least one disintegration agent, wherein said disintegration agent causes the rapid dispersion of said drug to said target area of said gastrointestinal tract.

44. The dosage form of any one of claims 37–39, wherein said enteric coating comprises a material that reacts with an enzyme present in said target area of the gastrointestinal tract to release said drug, said effervescent penetration enhancer, and said noneffervescent penetration enhancer.

45. The dosage form of claim 37, wherein said effervescent penetration enhancer comprises a pharmaceutically acceptable effervescent couple; said effervescent couple comprising an acid or equivalent thereof and a base or equivalent thereof.

46. The dosage form of claim 45, wherein said base is sodium bicarbonate.

47. The dosage form of claim 45, wherein said base or equivalent thereof is present in an amount equal to about two times the amount of said drug; and said acid is present in an amount approximately equimolar to said base.

48. The dosage form of claim 45, wherein said base or equivalent thereof is present in an amount equal to about three times the amount of said drug; and said acid is present in an amount approximately equimolar to said base.

49. The dosage form of claim 37, wherein said drug is a drug that displays poor bioavailability in said gastrointestinal tract.

50. A tablet for delivery of a therapeutically effective amount of a drug to a target area in the gastrointestinal tract of a mammal; comprising:
   (a) a therapeutically effective amount of a drug;
   (b) at least one effervescent penetration enhancer; wherein said at least one effervescent penetration enhancer is present in an amount sufficient to increase the penetration of said drug across said target area of said gastrointestinal tract to permit delivery of a therapeutically effective amount of said drug;
   (c) an enteric coating maintained over said drug; and said at least one effervescent penetration enhancer; wherein said enteric coating prevents the release of said drug and said at least one effervescent penetration enhancer until a time at which said tablet reaches said target area in said gastrointestinal tract;
   said tablet containing a biconcave zone central to two outer zones; wherein said drug and said effervescent penetration enhancer are located in said biconcave zone.

51. The tablet of claim 50, wherein said two outer zones contain a bioadhesive.

52. The dosage form of claim 1, wherein said effervescent penetration enhancer comprises a pharmaceutically acceptable effervescent couple comprising an acid and a base, wherein said acid of said effervescent couple is selected from the group consisting of citric, tartaric, amalic, fumeric, adipic, and succinic acids, and said base of said effervescent couple is selected from the group consisting of sodium bicarbonate, sodium carbonate, potassium bicarbonate, potassium carbonate and magnesium carbonate.

53. The dosage form of claim 1, wherein said acid is selected from the group consisting of citric, tartaric, amalic, fumeric, adipic, and succinic acids, and said base is selected from the group consisting of sodium carbonate, potassium carbonate, disodium hydrogen phosphate and sodium dihydrogen phosphate.

54. The dosage form of claim 1, wherein said effervescent penetration enhancer includes sodium bicarbonate and a weak acid, and said pH-adjusting substance includes sodium carbonate or potassium carbonate.

55. The tablet of claim 50, further comprising a non-effervescent penetration enhancer located in said biconcave zone.

56. The dosage form of claim 1, wherein said effervescent penetration enhancer comprises a pharmaceutically acceptable effervescent couple comprising an acid and a base, wherein said acid of said pH-adjusting substance is the same as said acid of said effervescent couple.

57. The dosage form of claim 1, wherein said effervescent penetration enhancer comprises a pharmaceutically acceptable effervescent couple comprising an acid and a base, wherein said base of said pH-adjusting substance is the same as said base of said effervescent couple.

58. The dosage form of claim 1, wherein said effervescent penetration enhancer comprises a pharmaceutically acceptable effervescent couple comprising an acid and a base, wherein said acid of said pH-adjusting substance is different from said acid of said effervescent couple.

59. The dosage form of claim 1, wherein said effervescent penetration enhancer comprises a pharmaceutically acceptable effervescent couple comprising an acid and a base, wherein said base of said pH-adjusting substance is different from said base of said effervescent couple.

* * * * *

UNITED STATES PATENT AND TRADEMARK OFFICE
CERTIFICATE OF CORRECTION

PATENT NO. : 6,350,470 B1
DATED : February 26, 2002
INVENTOR(S) : S. Indiran Pather et al.

It is certified that error appears in the above-identified patent and that said Letters Patent is hereby corrected as shown below:

Column 8,
Line 55, "Qc" should read -- Qs --.

Signed and Sealed this

Twenty-first Day of January, 2003

JAMES E. ROGAN
*Director of the United States Patent and Trademark Office*